US00PP24506P2

(12) United States Plant Patent
Korlipara

(10) Patent No.: US PP24,506 P2
(45) Date of Patent: May 27, 2014

(54) *ECHINACEA* PLANT NAMED 'VANILLA CUPCAKE'

(50) Latin Name: ***Echinacea* hybrid**
Varietal Denomination: 'Vanilla Cupcake'

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 13/694,808

(22) Filed: Jan. 8, 2013

(51) Int. Cl.
*A01H 5/00* (2006.01)

(52) U.S. Cl.
USPC ..... Plt./428

(58) Field of Classification Search
USPC ..... Plt./428
See application file for complete search history.

*Primary Examiner* — Anne Grunberg
(74) *Attorney, Agent, or Firm* — Klarquist Sparkman, LLP

(57) ABSTRACT

A new and distinct *Echinacea* plant named 'Vanilla Cupcake' characterized by large inflorescences with white to cream ray florets and light yellow lime disc florets, enlarged disc florets forming an anemone-type inflorescence, ray florets which are held horizontally when young, a short, mounding habit with high stem count, and high vigor.

1 Drawing Sheet

Botanical denomination: *Echinacea* hybrid.
Variety designation: 'Vanilla Cupcake'.

The present invention relates to a new and distinct cultivar of *Echinacea* and given the cultivar name 'Vanilla Cupcake'. *Echinacea* is in the family Asteraceae. The new cultivar is part of a planned breeding program for a series with compact habits and double "anemone"-type inflorescences. The exact parents of this selection are unknown, unnamed, proprietary interspecific hybrids.

Compared to *Echinacea* 'White Double Delight' (U.S. Plant Pat. No. 23,472), the new cultivar has larger inflorescences.

Compared to *Echinacea* 'Milkshake' (U.S. Plant Pat. No. 20,594), the new cultivar has larger inflorescences.

This new *Echinacea* cultivar is distinguished by:

1. large inflorescences with white to cream ray florets and light yellow lime disc florets,
2. enlarged disc florets forming an anemone-type inflorescence,
3. ray florets which are held horizontally when young,
4. a short, mounding habit with excellent stem count, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, was done in Canby, Oreg., and shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a two-year-old plant of *Echinacea* 'Vanilla Cupcake' growing in the trial bed in flower in full sun in late July in Canby, Oreg.

DETAILED PLANT DESCRIPTION

The following is a detailed description of the new *Echinacea* cultivar based on observations of two-year-old specimens growing in the trial beds in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The *Royal Horticultural Society Colour Chart,* $5^{th}$ edition.

Plant:

*Type*.—Herbaceous perennial.
*Hardiness*.—USDA Zones 4 to 9.
*Size*.—Grows to about 56 cm wide and 46 cm tall to top of inflorescences.
*Form*.—Basal clump, with about 25 stems from the base.
*Vigor*.—Excellent.
*Roots*.—Fibrous, with many downward growing and few laterals, ivory in color, Yellow White 158D, roots develop easily from cuttings from the crown.

Stem (flowering):

*Type*.—Ascending, with 1 to 6 inflorescences per stem.
*Size*.—To 10 cm to 18 cm tall to a terminal inflorescence and 8 mm wide at base.
*Internode length*.—1.5 cm to 2 cm.
*Surface texture*.—Strigose.
*Color*.—Yellow Green 146B.

Leaf (basal):

*Type*.—Simple.
*Shape*.—Ovate to lanceolate.
*Arrangement*.—Basal.
*Blade size*.—Grows to 10.5 cm long and 4 cm wide.
*Margins*.—Sparsely serrate.
*Apex*.—Acute.
*Base*.—Attenuate.
*Surface texture*.—Strigose on both sides.

*Venation*.—Pinnate, with 3 main veins from the base, Yellow Green 147D on both sides.

*Color*.—Topside, Green 137A, bottom side Green 137B.

*Petiole description*.—Grows to 10.5 cm long and 3 mm wide above the clasp, sparsely strigose, Yellow Green 146C.

Leaf (stem):

*Type*.—Simple.

*Shape*.—Lanceolate.

*Arrangement*.—Alternate.

*Blade size*.—Grows to 14 cm long and 5 cm wide.

*Margins*.—Entire to sparsely serrate.

*Apex*.—Acuminate.

*Base*.—Attenuate.

*Surface texture*.—Strigose on both sides.

*Venation*.—Pinnate, with 3 main veins from the base, Yellow Green 147D on both sides.

*Color*.—Topside, Green 137A, bottom side Green 137B.

*Petiole description*.—On all but upper leaves, clasping, grows to 2 cm long and 6 mm wide above the clasp, strigose, topside, Green 137A on sides and Yellow Green 146C in center, bottom side Green 137B on sides and 147C in center.

Inflorescence:

*Type*.—Composite on terminal stalked heads.

*Number of flowering stems from the ground*.—About 25.

*Flowering stem*.—Grows to 29 cm tall from the base of the plant to the terminal inflorescence and can grow to 14 cm long from the top stem leaf to the base of an inflorescence; branched with 1 to 6 inflorescences per stem; diameter growing to 7 mm wide near the inflorescence; strigose; Yellow Green 146B.

*Size*.—Grows to 9.5 cm wide and 6.5 cm deep as disc enlarges.

*Form*.—Ray florets held slightly reflexed, mature disc is conic.

*Immature inflorescence*.—Grows to 3.5 cm wide and 2.3 cm deep, ray florets held at a 40 degree angle from the horizontal and rolled up so only the back color shows, closest to Yellow Green 150D, disc color Yellow Green 144A.

*Ray florets*.—Without pistil or stamen, about 23 to 33 in number, grow to 52 mm long and 13 mm wide, oblanceolate with the tip two-toothed to two-lobed, curling back from sides when mature, lobes grow to 7 mm long and 4 mm wide, tips acute, margins entire, base attenuate, glabrous on both sides; top side White 155A becoming Green White 157A when all disc florets are fully open, bottom side White 155A becoming Yellow White 158B with veins and base Yellow Green 144A.

*Disc*.—Flat becoming conic, growing to 50 mm deep and 55 mm wide with maturity, Yellow Green 144A when disc florets are closed to Yellow 4C when disc florets are open.

*Disc florets*.—To about 400 in number, each with 1 pistil and 4 stamen, grow to 20 mm long and 13 mm wide, each with one persistent, very stiff linear bract (8 mm long with top 5 mm Greyed Yellow 161A blending to 3 mm Yellow Green 144B on bottom); corollas to 18 mm long and 7 mm wide, tubular at base (to 3 mm long and 1.5 mm wide, Yellow Green 144A) then opens to a 3-toothed fan or 3-toothed fan and 1 side lobe, fan is oblanceolate and grows to 12 mm long and 5 mm wide with teeth 1 to 4 mm deep and 1 mm wide, (side lobe linear, cut to the tube, to 12 mm long and 1 mm wide); margins entire, tips acute, bases attenuate, glabrous on both sides, topside young florets White 155A with tips Yellow Green 144A, bottom side Yellow Green 145D, older florets both sides Yellow 8D; pistil 9 mm long, ovary 4.5 mm long, White NN155A with top Yellow Green 144A, style 4.5 mm long White 155A, 2-branched stigma spreading, Yellow 8D; stamen 4 mm long, filaments 3 mm long, threadlike, White 155A, anthers none, no pollen, male sterile.

*Phyllaries*.—In 3 leafy series, area grows to 30 mm wide and 7 mm deep, lobes lanceolate in shape, reflexed, grow to 7 mm long and 3 mm wide, both sides Yellow Green 147B, margins strigose, tip acute, strigose.

*Receptacle*.—Grows to 10 mm wide and 14 mm deep, White NN155B.

*Bloom period*.—July through October in Canby, Oreg.

*Fragrance*.—Slight, floral.

*Lastingness*.—Each inflorescence lasts about three weeks in Canby, Oreg.

Seeds: None seen.

Fertility: Poor.

Disease and pests: No pests or diseases have been observed on plants grown under commercial conditions in Canby, Oreg. No resistances are known.

I claim:

1. A new and distinct *Echinacea* plant as herein illustrated and described.

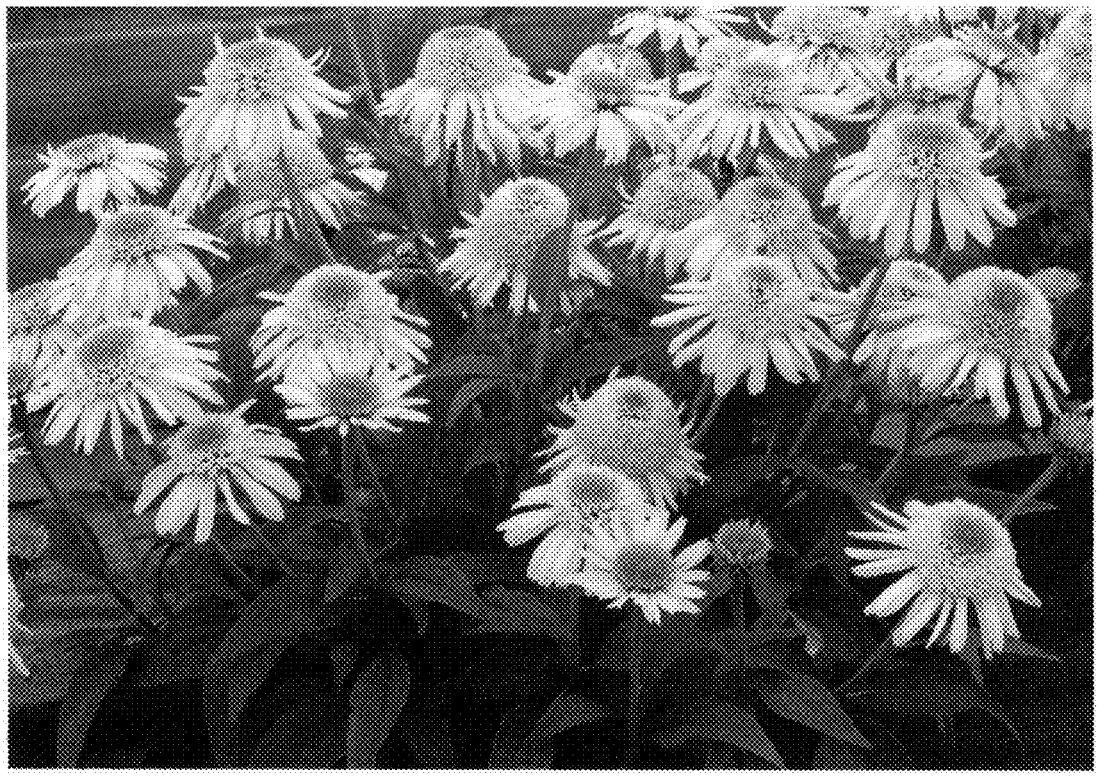

* * * * *